United States Patent [19]

Cardenas et al.

[11] Patent Number: 4,697,600
[45] Date of Patent: Oct. 6, 1987

[54] METHOD FOR OBTAINING TISSUE AND CELLS BY FINE NEEDLE ASPIRATION FOR CYTOLOGY/BIOPSY AND KIT RELATING TO THE SAME

[76] Inventors: Frank Cardenas, 6538 Crosswords Dr., Falls Church, Va. 22044; Ellsworth J. Stay, 1504 Laburnum St., McLean, Va. 22101

[21] Appl. No.: 873,051

[22] Filed: Jun. 4, 1986

Related U.S. Application Data

[63] Continuation of Ser. No. 547,644, Nov. 1, 1983, abandoned.

[51] Int. Cl.[4] ............................................. A61B 10/00
[52] U.S. Cl. ..................................................... 128/753
[58] Field of Search ............... 128/749, 752, 753, 760, 128/763, 764, 770

[56] References Cited

U.S. PATENT DOCUMENTS

| 2,822,808 | 2/1958 | Boone | 128/749 V |
| 3,200,813 | 8/1965 | Christalois | 128/753 |
| 4,112,925 | 9/1978 | Sullivan | 128/760 |
| 4,249,541 | 2/1981 | Pratt | 128/753 |
| 4,436,098 | 3/1984 | Kaufman | 128/770 |
| 4,441,951 | 4/1984 | Christinger | 128/764 X |

Primary Examiner—Edward M. Coven
Attorney, Agent, or Firm—Finnegan, Henderson, Farabow, Garrett & Dunner

[57] ABSTRACT

The method involves obtaining tissue and cells for biopsy by fine needle aspiration comprising the steps of: (a) inserting one end of a fine, hollow needle into an area of body tissue; (b) inserting the protruding end of the fine, hollow needle into an evacuated container with a pre-established vacuum; (c) continuously suctioning tissue and cell samples through the fine, hollow needle into the container; (d) withdrawing the fine, hollow needle from the body tissue; and (e) preserving the tissue and cell samples in the container. A tissue needle aspiration biopsy kit is also disclosed having component parts capable of being assembled to provide means for aspiration biopsy of soft body tissue and cells, kit comprising a combination of (a) at least one fine, hollow needle having one end adapted for insertion into a vacuum container and the other end adapted for introduction into an area of the body; (b) at least one evacuated container adapted to be affixed to the hollow needle with a pre-established vacuum sufficient so as to cause a suction of the tissue and cells through the fine, hollow needle into the container; and (c) a physiological solution to preserve the tissue and cell samples collected in the container.

36 Claims, 1 Drawing Figure

METHOD FOR OBTAINING TISSUE AND CELLS BY FINE NEEDLE ASPIRATION FOR CYTOLOGY/BIOPSY AND KIT RELATING TO THE SAME

This application is a continuation of application Ser. No. 547,644, filed Nov. 1, 1983, abandoned.

BACKGROUND OF THE INVENTION

The present invention relates to a method for obtaining tissue and cells for biopsy using a novel fine needle aspiration technique. This technique is suitable for sampling both discrete tumors and vague areas of thickening of soft tissues. This invention modifies the present techniques of fine needle aspiration by simplifying the aspiration procedure, improving the collection and protection of the specimen, and increasing the range of sampling sites and amount or quantity of obtained tissue and cells.

Fine needle aspiration cytology is currently gaining in popularity as a medical technique for sampling body tissues suspected of being malignant. The procedure of the prior art involved the use of a fine needle coupled with a suction device to draw a tissue sample into the needle. The prior art suction device, generally a syringe, is held in a frame-type apparatus or "gun" device. Examples of such frame-type apparatus are those available under the marks "Cameco ®" and "Aspir gun ®." A frame-type apparatus of this sort is frightening when seen from a patient view-point; being approached with this device for a cytology aspiration/biopsy can increase the stress involved in an already distressing event which results usually in the patient's reluctancy to return for re-evaluations later on. This aspect of the technique is especially important dealing with breast pathology when numerous aspiration/biopsy may be necessary for the follow-up of the patients over a period of several months or even years.

The prior art technique drew a tissue sample into a hollow needle. The vacuum used for drawing the tissue into the needle was then released and the needle withdrawn from the area being sampled. The tissue sample was contained within the barrel of the needle. If the tissue sample proceeded into the barrel of the vacuum source, such as a syringe, the procedure was deemed a failure due to (1) the drying of the tissue that occurred when the tissue was drawn into the barrel of the syringe; and (2) the difficulty of retrieving the tissue from the barrel of the syringe. The small amount of tissue thus contained in the needle was expelled and placed on glass slides. Only discrete "tumors" would be properly sampled with the original method. Cytological examinations could be conducted on the sample affixed to one slide or, as the examination is usually conducted, the sample is divided into 2 to 4 slides.

It has been emphasized in the medical literature that the prior art procedure was limited to use when a discrete tumor or isolated cystic mass was found during the examination of the patient. It is also found, in the experience of many physicians, that the prior art procedure is relatively uncomfortable, if not painful, for patients and psychologically detestable for the female patient with breast pathology.

The new method of fine needle cytology aspiration/biopsy of the present invention has advantages from the medical standpoint. The method of the present invention is more efficient and easier to perform than the other methods of fine needle aspiration biopsy currently in use. The individual components of equipment used in this method are familiar to most medical personnel and patients. The method of the present invention offers better control and easier maneuverability of the fine needle aspiration equipment than was available with the heavier, frame-type apparatus or even the regular syringe when used for vacuum purposes.

Also, in the experience of the inventors, the present invention has a lower incidence of "false negative" readings (readings where the sample is indicative of benign tissue while the tissue is in fact malignant) than the prior art procedures. A medically acceptable low level of "false positive" readings (readings where the sample is indicative of malignant tissue when the tissue is in fact benign) has also been found with this technique.

In addition, the method of the present invention offers a radius of action allowing for a 360 degree examination of an area covered by several passes of the needle. The prior art method only allowed for examination of one particular mass lesion, rather than a wide range of tissue. This capability of the new technique results in more dependable sampling and examination of the tissue obtained, producing far fewer "false negative" diagnoses. The method of the present invention has particular significance in the breast in regard to areas of thickening. Areas of this type were not suitable for examination using the method of the prior art.

The method of the present invention also allows for use when a lump or tumor is visualized by radiographic, sonagraphic, heat-sensing or mammographic means but is not palpable by a physician. This advantage arises from the multiple needle passes that may be made with the new method. The use of multiple needle passes increases the chance of actually sampling unfelt and small tumors.

The method of cytology aspiration/biopsy of the present invention also has advantages from the patient viewpoint. This aspiration/biopsy method can be performed quickly, usually in two to three minutes. The quickness of the procedure, as well as the patient's familiarity with the equipment, helps to lessen the psychological trauma associated with an extended procedure.

The method of the prior art involved the use of "short, jackhammer-like strokes" of the the needle, in addition to manual suction, to force tissue and cell samples from tumors into the barrel of the needle. Frable, W. J., "Fine Needle Aspiration Biopsy Clinical Applications", Surgical Rounds, March 1982, pps. 40–44, 51. In addition to inducing pain, a psychological trauma could be induced by subjecting a patient to this type of procedure without the benefits of some form of local anesthesia. The cytology aspiration/biopsy method of the present invention eliminates a measure of both physical and mental trauma of this sort. The present invention does not utilize "short, jackhammer-like strokes" but rather uses smooth passages through the tissue. The equipment, being similar to those implements used in drawing blood for testing, and technique are more familiar to patients and thus less traumatic. Also, the use of a local anesthesia for the skin overlying the tissue to be sampled gives more reassurance to the patient of having less discomfort.

Further, the method disclosed in the present invention and materials used in this technique are simple and more efficient in localizing and collecting samples of cells and tissues than those used in the prior art fine needle aspiration biopsy techniques. The prior art materials consist of a large syringe (generally 20 cc.), usually held in a large metal frame. Although 20 cc. of specimen was never withdrawn from a patient with the prior art method, indeed no part of the specimen was ever intended to enter the syringe itself, the larger size of the syringe was dictated by the larger metal frame for manual suction of the tumor cells. In contrast, the materials used in the method of the present invention are familiar materials, used traditionally in clinical laboratories for withdrawing blood from a patient.

U.S. Pat. No. 3,200,813 discusses a previously used method of sampling certain body tissues, in particular fat globules. This method involved injecting saline, through a sterile needle, into the body, followed by the application of a vacuum through the needle to withdraw the injected saline and the dislodged fat globules into a collecting vessel. The needle was then removed and the fat globules stored in the saline in the collection vessel.

The present invention differs from this prior art method in that no fluid is injected into the area of tissue to be sampled. It has been found that such injection of foreign substances into tissue for the purpose of dislodging body substances to be sampled could be harmful in patients with malignant tumors. Further, body substances or cells collected and subsequently stored in saline solution are not adequately preserved for a proper cytological examination later on.

SUMMARY OF THE INVENTION

The present invention overcomes the disadvantages of the prior art by providing for a novel method for obtaining both tissue and cells for biopsy of soft tissues and a kit for the simplified use with the same as more fully described hereinbelow.

In accordance with the present invention, a method for obtaining tissue and cells for needle aspiration biopsy is disclosed comprising the steps of: (a) inserting one end of a fine, hollow needle into an area of body tissue; (b) inserting the protruding end of the fine, hollow needle into an evacuated container with pre-established vacuum; (c) continuously suctioning tissue and cell samples through the fine, hollow needle into the container; (d) withdrawing the fine, hollow needle from the body tissue; and (e) preserving the tissue and cell samples in the container.

In further accordance with the present invention, a method for obtaining samples of tissue and cells from breast tissue for biopsy is disclosed, comprising the steps of: (a) locating vague areas of diffuse thickening in the breast tissue; (b) penetrating the skin of the breast with the front end of a fine, hollow needle; (c) moving the fine, hollow needle into a first area of the breast containing the area of thickening; (d) inserting the protruding end of the fine, hollow needle into an evacuated container with a pre-established vacuum; (e) continuously suctioning tissue and cell samples through the fine, hollow needle into the evacuated container while passing the needle at least once through the first area of thickening; (f) withdrawing the fine, hollow needle to the layer of the body under the skin at the site of insertion without losing the vacuum in the container; (g) reinserting the fine, hollow needle into a subsequent area of thickening to produce sampling of tissue different from the first area of penetration of the needle; (h) continuously suctioning tissue and cell samples through the fine, hollow needle into the evacuated container while passing the needle at least once through the subsequent area of thickening; (i) withdrawing the fine, hollow needle from the breast tissue; and (j) preserving the tissue and cell samples in the container.

Also in accordance with the present invention, a tissue biopsy kit is disclosed having component parts capable of being assembled in a few seconds to provide means for biopsy of soft body tissues and cells, the kit comprising a combination of: (a) at least one fine, hollow needle having one end adapted for insertion into a vacuum container and the other end adapted for introduction into an area of the body; (b) at least one evacuated container adapted to be affixed to the fine, hollow needle with a pre-established vacuum sufficient so as to cause a suction of the tissue and cells through the fine, hollow needle into the container; and (c) a physiologic solution to preserve the tissue and cell samples collected in the container.

It is to be understood that both the foregoing general description and the following detailed description are exemplary and explanatory only and are not restrictive of the invention as claimed.

DESCRIPTION OF THE PREFERRED EMBODIMENTS

Figure 1:
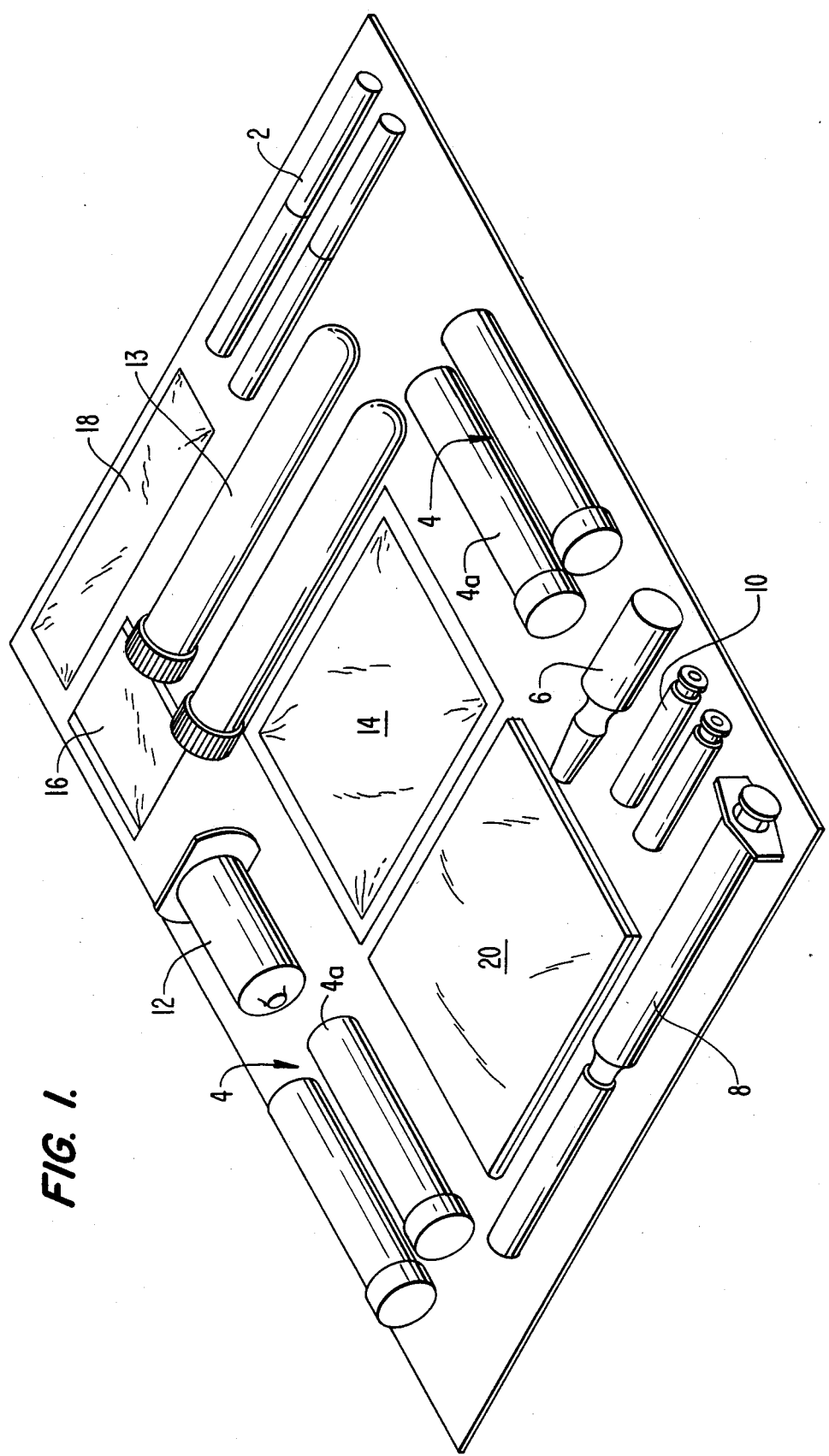
FIG. 1 is a depiction of a preferred tissue biopsy kit of the present invention.

Reference will now be made in detail to the present preferred embodiments of the invention. In accordance with the invention, a method for obtaining cells and tissue for needle aspiration biopsy comprises the steps of: (a) inserting one end of a fine, hollow needle into an area of body tissue; (b) inserting the protruding end of the fine, hollow needle into an evacuated container with a pre-established vacuum; (c) continuously suctioning tissue and cell samples through the fine, hollow needle into the container; (d) withdrawing the fine, hollow needle from the body tissue; and (e) preserving the tissue and cell samples in the container.

This method is suitable for obtaining tissue and cells for biopsy from any body tissues accessible through the degree of penetration of the needle and is particularly suitable for obtaining tissue and cells from soft body tissues. As used hereinafter, the term "body tissue" shall connote any type of tissue, cell or fluid contained in a body, including but not limited to malignant and benign tumors, cysts, swellings, thickenings, cavities and fluids.

The method of the present invention, while particularly useful in obtaining tissue for biopsy from any region of soft body tissue, is especially suitable for obtaining needle biopsy from the breasts. Other areas of soft body tissue for which this method is particularly suited include, but are not limited to, thyroid, subcutaneous tissues and lymph nodes. This method may also be used to obtain fluid from the thoracic and abdominal cavities for cytology and the amniotic cavity for studies of amniotic fluid.

Typically, a fine, hollow needle, with an attached barrel and holder, intended for use in withdrawing blood from veins is suitable. Preferably, such a venipuncture needle is used. More preferably, a venipuncture needle having a gauge ranging from 20 gauge to 22 gauge is used. Most preferably, a 22 gauge venipuncture needle is used. A suitable 22 gauge venipuncture needle with attachable holder and barrel is available from Benton-Dickinson.

The needle may be attached to a plastic cylinder or holder so as to facilitate the grasping of the needle and the vacuum container together in one hand. After the needle with plastic cylinder attached has penetrated the layers of the body under the skin, the protruding, back end of the needle is introduced in the vacuum container perforating the rubber top/cap that seals the container with vacuum.

In addition, the fine needle may be of different lengths to penetrate from the skin to the area to be biopsied. The length of the needle will vary according to the location of the region of body tissue into which the needle is to be inserted. For breast and cytology/aspiration biopsy of any other soft tissue the choice of the needle length is one generally made by a person of ordinary skill in the art.

Any medically suitable vacuum container may be used to supply the suction force necessary to extract the tissue and cell samples through the fine needle into the vacuum container, which container then serves as a collection receptacle for the tissue and cell samples. Preferably, a glass tube, with one closed rounded end, which has vacuum and is closed on the other end with a sterile rubber membrane is used. Most preferably, a container known as a "vacutainer ®" is used. Vacutainers ® are available, for example, from Benton-Dickinson.

The physiological solution, serving as a preservative, is used to preserve the tissue and cell samples in the container may be any medically suitable, balanced salt solution. Preferably, the physiological solution is a balanced salts solution, for example, a TIS-U-SOL solution, obtained from Travenol. The physiological solution may be inserted into the container before the protruding end of the fine, hollow needle is inserted into the container or may be added to the tissue and cell samples once they are collected in the container.

If blood is mixed with the tissue and cell samples, an anticoagulant may be used. A vacuum tube with an anticoagulant coated on the sides may be used. Preferably, the anticoagulant is present in the vacuum container before the suctioning of tissue and cell samples into the container to prevent coagulation of the blood which will interfere with the cytopathologic techniques to be performed on the specimen. A preferred anticoagulant is sodium heparin, currently available, for example, in a vacutainer ®, from Benton-Dickinson.

By using the cytologic preservation method of the present invention, examination of the tissue and cell samples may be delayed for up to 3 to 5 days. If cytological examination is delayed, the tubes with the tissue and cell samples and preservative are refrigerated.

Cytological examination of the tissue obtained may be done by any medically acceptable method. "Cellblock" examination will provide additional information to the cyto-pathologist. The numerous pieces of tissue found in the collecting container may be used to prepare a cell block. To form a cell block, the preservative fluid is centrifuged to separate the preservative from the cells. For cytologic examination the tissue and cell samples may also be separated from the preservative by filtration. A method of filtration that is acceptable is, for example, the Gelman Filtration Procedure. The remaining fluid may be examined using any standard staining technique. Such staining procedures include, but are not limited to, the Papanicolaou staining technique or the Wright staining technique.

In using the method of the present invention, the area from which the tissue is to be obtained is identified. This may be done by any common medical means such as palpation, and including but not limited to, identification of a nodule, lump, thickening or cyst, or identification by radiographic or sonagraphic or heat-sensing means.

When the needle is inserted into the area to be biopsied, it is generally necessary for a determination to be made that the needle is in the correct place. If the area to be biopsied is a palpable nodule or lump, the needle will be felt to enter the area, and the resistance of nodule or lump should be felt in correspondence to passage of the needle. In other situations, radiography may be used to follow the progress and depict the location of the needle in reference to the area from which the sample is to be obtained Using the method of the present invention, it is possible to hold and control both the needle and the evacuated container with one hand using a "light touch" since the manual aspiration of the other techniques is eliminated. This is especially true when the container of a type known as a "vacutainer ®" is used with a holder attached to the needle. When, as in the preferred embodiment, a needle and a holder are used, the protruding end of the needle may be inserted through the rubber membrane of the vacutainer ® with a single motion of the thumb of the hand holding the vacutainer. The insertion of the protruding end of the needle into the container will cause a suctioning force to be created through the hollow needle. This force will draw tissue or fluid samples through the needle and into the container.

The suctioning force should be maintained until sufficient samples are obtained. If the area being sampled is a cyst, the suctioning force should be maintained until all fluid has been removed from the cyst and resides within the container. At that point, the area being sampled should be re-examined to ensure that no tumor associated with the cyst is present and has not been sampled.

In further accordance with the invention, a method for obtaining tissue and cells from breast tissue for needle aspiration biopsy is disclosed, comprising the steps of (a) locating vague areas of diffuse thickening in the breast tissue; (b) penetrating the skin of the breast with one end of a fine, hollow needle; (c) moving the fine, hollow needle into a first area of the breast containing the area of thickening; (d) inserting the protruding end of the fine, hollow needle into an evacuated container with a pre-established vacuum; (e) continuously suctioning tissue and cell samples through the fine, hollow needle into the evacuated container while passing the needle at least once through the first area of thickening; (f) withdrawing the fine, hollow needle to the layer of the body under the skin at the site of insertion without losing the vacuum in the container; (g) re-inserting the fine, hollow needle into a subsequent area of thickening to produce sampling of tissue different from the first area of penetration of the needle; (h) continuously suctioning tissue and cell samples through the hollow needle into the evacuated container while passing the needle at least once through the subsequent area of thickening; (i) withdrawing the fine, hollow needle from the breast; and (j) preserving the tissue and cell samples in the container.

Traditional methods of fine needle aspiration have only been useful when a cyst, tumor or lump has been identified in breast tissue. However, a method of obtaining tissue for biopsy has been sought for situations when a malignancy has been suspected in a breast containing vague areas of nodularity or thickening. The method of the present invention allows for a method of obtaining tissue and cell specimens from breast tissue when vague areas of nodularity or thickening are found and it has been determined that a tissue sample is necessary.

In the method of the present invention, the hollow needle is inserted into the first vague area of nodularity in one quadrant of the breast. The protruding, back end of the needle is, in the preferred embodiment, inserted through a rubber membrane into the evacuated container as previously described. The insertion of the protruding end of the hollow needle into the evacuated container causes a suctioning force to be applied through the hollow needle on the tissue located in the first vague area of nodularity.

After tissue and cell samples have been obtained from the first vague area of nodularity, the needle with attached container is withdrawn slowly until the point of the needle approaches the skin. At this point, with the point of the needle still embedded in the breast tissue, the needle is reinserted into a second area of vague nodularity in the same quadrant of the breast.

The method of withdrawing and reinserting the needle into new areas of vague nodularity is repeated until all identified areas of vague nodularity are sampled. If the areas of vague nodularity have been identified as extending throughout the breast tissue, the method of withdrawing and reinserting the needle may be continued through a 360° arc in the quadrant of the breast which is being sampled. When the sampling is complete, the hollow needle is withdrawn completely from the breast tissue. Additional quadrants may be sampled using additional hollow needles and evacuated containers.

The physiologic solutions, fine, hollow needles and evacuated containers preferred for use in this method are the same as those suitable for and preferred for use in the above method. The filtering and centrifuging steps suitable for use in cytological preparation in the above method are also suitable for use in this method.

In further accordance with the present invention, a tissue biopsy kit is disclosed having component parts capable of being assembled in a few seconds to provide means for biopsy of body tissues, the kit comprising a combination of: (a) at least one fine, hollow needle, having one end adapted for insertion into an area of the body and the other end adapted for introduction into an evacuated container; (b) at least one evacuated container adapted to be affixed to the back end of the fine, hollow needle with a pre-established vacuum sufficient so as to cause a suction force to be exerted through the fine, hollow needle sufficient to cause a suction of tissue and cells through the fine, hollow needle into the evacuated container; and (c) physiologic solution to preserve the tissue and cell samples collected in the container. A preferred tissue biopsy kit is shown in FIG. 1.

In the preferred embodiment, the tissue biopsy kit comprises one fine, hollow needle 2 and four evacuated containers 4, two of which contain an anticoagulant 4a.

The tissue biopsy kit disclosed in the present invention may further comprise, in combination, a vial or ampoule of anesthetic 6. Such anesthetic must be suitable for anesthetizing an area of the skin of the body into which the needle is to be inserted and the tissue sample withdrawn. Suitable anesthetics include, but are not limited, to local anesthetics such as xylocaine. Xylocaine may or may not contain epinephrine and may be in a concentration 0.5%–1.0%. Preferably, the local anesthetic to be used in the tissue biopsy kit is 1% xylocaine without epinephrine, obtained, for example, from ASTRA of Worcester, Massachusetts.

The tissue biopsy kit of the present invention may also further comprise at least one syringe 8, with a capacity of 3 to 10 c.c., and preferably 3 c.c., with 2 needles attachable thereto, said syringe (as in page 25 cl. 28.) by which the anesthetic is transferred from its container to the patient. Preferably, a hollow needle 10 is attached thereto for the purpose of injecting the anesthetic. The hollow needles may have a gauge between 22 and 27, and preferably are 27 gauge needles.

The needles, evacuated container and holder 12 suitable for use in the tissue biopsy kit are the same as those which are suitable for use in the method for obtaining tissue for biopsy described above. Preferably there will be at least one 22-gauge needle 2, adapted to fit the evacuated container apparatus 4, for performing the biopsy. The containers 4 of the tissue biopsy kit are preferably evacuated glass tubes. At least one of the evacuated tubes 4a of the tissue biopsy kit may contain an anticoagulant. The anticoagulant of the tissue biopsy kit may be any suitable for use in this method, including, but not limited to, sodium heparin.

Suitable physiological solutions 13 to serve as preservatives for use in the tissue biopsy kit have also been described above in connection with the method for obtaining tissue for biopsy. Preferably, the physiological solution to be used in the kit is a balanced salt solution.

The tissue biopsy kit may further comprise at least one gauze sponge 14 adapted to arrest the effusion at, or dry the site of, the biopsy subsequent to the removal of the needle from the biopsy site. The most common sizes of gauze sponges are 4 inches by 4 inches and four ply, or 2 inches by 2 inches and eight ply, but the invention herein described does not contemplate these two examples as limitations thereto.

The tissue biopsy kit may further comprise at least one alcohol-saturated pad 16. Such an alcohol saturated pad includes swabs, which may be used to cleanse the skin at the site of biopsy prior to the beginning of the biopsy procedure.

The tissue biopsy kit may further comprise at least one adhesive bandage 18, which may be used to protect the biopsy site from infection or prevent leakage from the biopsy site or the site of anesthetic injection after biopsy procedure is completed.

The tissue biopsy kit may further comprise at least one sterile fenestrated drape 20, which may be used to shield an area of the patient's body during the biopsy procedures described above from contamination.

The following examples were designed to elucidate the teachings of the present invention, and in no way limit the scope of the invention. Various other modifications and equivalents of the examples will readily suggest themselves to persons of ordinary skill in the art, particularly after the issuance of this patent, without departing from the spirit or scope of the present invention.

EXAMPLE 1

This example illustrates the use of the method of this invention in obtaining tissue for biopsy from breast tissue. The equipment used in this example consisted of a 22 gauge venipuncture (Benton-Dickinson) needle with an attached plastic barrel and holder, a vacutainer tube (Benton-Dickinson), red top, and a preservative (TIS-U-SOL solution, Travenol).

The patient was placed in a supine position. The area of interest was cleansed with an alcohol swab. Local anesthesia was induced with approximately 3 cc's of 1% xylocaine to include the skin and underlying subcutaneous tissue and superficial breast tissue. The area for study in the breast was grasped with one hand in a position suitable for needling, drawing the area to be sampled away from the chest wall. With the vacutainer tube in the barrel of the venipuncture needle, but not punctured, the skin was entered with the venipuncture needle.

When the area of breast to be studied was entered, the vacutainer tube was punctured by the venipuncture needle by use of simple pressure with the thumb on the vacutainer tube and a vacuum was formed. Numerous passes were made through the breast tissue to be sampled in many directions and at varying depths. Both fluid and tissue fragments were drawn into the vacutainer tube by the vacuum with each pass of the needle. The needle and attached tube were withdrawn from the breast, and simple pressure was placed over the biopsy site with a gauze.

The vacutainer tube was then opened and approximately 5 cc. of preservative were placed in the tube. The tube was re-covered and placed in the refrigerator. The cytopathology laboratory prepared, stained and diagnosed the sample in the tube. If blood had been admixed with the specimen an anticoagulant in a "green top" container could have been added along with the preservative. The period of time that may lapse between the biopsy and the cyto-preparation is variable (up to 3-5 days), but the tube should remain in the refrigerator until it is taken to the laboratory.

Cyto-preparation

The cytotechnologist evaluated the suspended aspirated material for pieces of tissue which were adequate to prepare a cell block. The Gelman Filtration Procedure was used to prepare the remaining fluid, followed by the Papanicolaou staining technique.

EXAMPLE 2

198 patients were examined for breast masses, cysts, or vague areas of nodularities or thickening in the breast. Of these, 75 patients underwent surgical biopsy following fine needle aspiration cytology conducted by the method of Example 1. The results are shown in Table 1.

TABLE I

| Class | Description | No. of Patients Undergoing Surgical Biopsy | No. of Positive (Malignant) Surgical Biopsies | |
|---|---|---|---|---|
| CLASS V | Virtually diagnostic of malignancy: | 13 | 13 | |
| CLASS IV | Highly suspicious of malignancy: Surgical Biopsy necessary to establish diagnosis | | | Malignancy highly probable |
| CLASS III | Suspicious of malignancy: Surgical Biopsy necessary to establish diagnosis | 22 | 13 | |
| CLASS IIB | Atypical cells: Consultation with pathologist necessary before making final decision | | | Questionable situation |
| CLASS IIA | Reactive - inflammatory: Follow-up every three to six months | 40 | 5 | Non-malignant highly probable |
| CLASS I | No atypical cells: Routine follow-up | | | |

The findings by fine needle aspiration cytology are summarized in Table I which also summarizes the findings on surgical biopsy. The correlation between the aspiration cytology and surgical biopsy was 96.0% (72 of 75 patients). There were no false positives (13 Class V cytologies - 13 malignant lesions found on biopsy). There were five false negatives of which two of the specimens were diagnosed as atypical cytology (IIB), in which the pathologist recommended biopsy, therefore true false negative rate 3/75 (4%). Both of these cases were confirmed by biopsy as malignant. The other three were true false negative in that the cytology were Class I or IIA (no atypical cells) and in which the biopsy revealed malignancy. These latter case were most likely due to missing the lesion, a problem with all needle aspiration techniques, but highly reduced with the present technique.

It will be apparent to those skilled in the art that various modifications and variations can be made in the methods of the present invention without departing from the scope or spirit of the invention. Thus, it is intended that the present invention cover the modifications and variations of the invention provided they come within the scope of the appended claims or their equivalents.

What is claimed is:

1. A method for obtaining tissue and cells for needle aspiration biopsy comprising the steps of:
    (a) inserting one end of a fine, hollow needle into an area of body tissue;
    (b) inserting the protruding end of said fine, hollow needle into an evacuated container with pre-established vacuum;

(c) continuously suctioning tissue and cell samples through said fine, hollow needle into said container without injection any substance, wherein said tissue and cell samples remain in contact with other cells and tissues which are normally adjacent to said tissue and cell samples until said tissue and cell samples are dislodged by the suctioning force;

(d) withdrawing said fine, hollow needle from said body tissue; and (c) preserving said tissue samples in said container.

2. The method of claim 1 wherein said method of obtaining tissue and cells for biopsy includes the step, before insertion of the fine, hollow needle into the area of body tissue, of anesthetizing the skin of said area.

3. The method of claim 1 wherein said hollow needle is inserted into a fluid-filled cyst.

4. The method of claim 1 wherein said hollow needle is inserted into suspicious areas of thickened tissue and multiple passes through said area of body tissue are made with said hollow needle.

5. The method of claim 1 wherein said preserving of said tissue and cell samples occurs when a preservative is added to said container after collection of said tissue and cell samples.

6. The method of claim 1 wherein said preservative is added to said container prior to insertion of said protruding end of said hollow needle into said container.

7. The method of claim 1 wherein said method of obtaining tissue for biopsy also includes the step of incorporating, after preserving said tissue and cell samples in said container, said tissue and cell samples for cytology, said tissue and cell samples into a cell block for cytological examination and said tissue and cell samples for regular histologic examination of the tissue if large tissue samples are obtained.

8. The method of claim 1 wherein said hollow needle is a venipuncture needle.

9. The method of claim 8 wherein said venipuncture needle is between 20 and 22 gauge.

10. The method of claim 8 wherein said venipuncture needle is 22 gauge.

11. The method of claim 1 wherein said area of body tissue into which said hollow needle is inserted is breast tissue containing tumors or breast tissue with areas suspicious of containing tumors.

12. The method of claim 1 wherein said evacuated, sterile container is a glass tube with one rounded glass end and the opposite end covered with a rubber membrane.

13. The method of claim 12 wherein said suctioning of tissue samples occurs when the protruding end of said hollow needle punctures said rubber membrane of said evacuated vacuum container.

14. The method of claim 5 wherein said tissue and cell samples are separated from the preservative prior to cytological examination.

15. The method of claim 1 wherein said evacuated container contains an anticoagulant.

16. A method for obtaining tissue and cells from breast tissue for needle aspiration biopsy, comprising the steps of:

(a) locating vague areas of diffuse thickening in said breast tissue;

(b) penetrating the skin of the breast with the front end of a fine, hollow needle;

(c) moving said fine, hollow needle into a first area of said breast containing said area of thickening;

(d) inserting the protruding end of said fine, hollow needle into an evacuated container with pre-established vacuum;

(e) continuously suctioning tissue and cell samples through said fine, hollow needle into said evacuated container while passing said needle at least once through said first area of thickening without injecting any substance, wherein said tissue and cell samples remain in contact with other cells and tissues which are normally adjacent to said tissue and cell samples until said tissue and cell samples are dislodged by the suctioning force;

(f) withdrawing said fine, hollow needle to the layer of the body under the skin at the site of insertion without losing said vacuum in the container;

(h) reinserting said fine, hollow needle into a subsequent area of thickening to produce sampling of tissue different from the first area of penetration of the needle;

(h) continuously suctioning tissue and cell samples through said fine, hollow needle into said container while passing said needle at least once through said subsequent area of thickening;

(i) withdrawing said fine, hollow needle from said breast tissue; and (j) preserving said tissue and cell samples in the container.

17. The method of claim 16 wherein said method for obtaining tissue and cells from breast tissue for needle aspiration biopsy includes the step, before penetrating the skin of the breast with the fine, hollow needle, of anesthetizing the skin of said breast.

18. The method of claim 16 wherein said method of obtaining tissue for biopsy further includes the step of incorporating, after preserving said tissue and cell samples in said container, said tissue and cell samples for cytologic examination, said tissue and cell samples into a cell block for cytological examination, and said tissue and cell samples for histologic study if large tissue fragments are obtained.

19. The method of claim 16 wherein said hollow needle is a venipuncture needle.

20. The method of claim 19 wherein said venipuncture needle is between 20 and 22 gauge.

21. The method of claim 19 wherein said venipuncture needle is 22 gauge.

22. The method of claim 16 wherein said evacuated container is a glass tube with one rounded glass end and the opposite end covered with a rubber membrane.

23. The method of claim 16 wherein multiple sites in said breast are sampled.

24. The method of claim 23 wherein said sampling of said multiple sites in said breast is done in a 360° arc.

25. A tissue biopsy kit having component parts capable of being assembled to provide means for needle aspiration biopsy of soft body tissues and cells, said kit comprising a combination of:

(a) at least one fine, hollow needle having one end adapted for insertion into a vacuum container and the other end adapted for introduction into an area of the body;

(b) at least one evacuated container adapted to be affixed to said fine, hollow needle with a pre-established vacuum sufficient so as to cause a suction of said tissue and cells through said fine, hollow needle into said container without the prior injection of any substance, wherein said evacuated container is a means for providing a suctioning force capable of continuously suctioning tissue and cells and wherein said tissue and cells remain in contact with other cells and tissue which are normally adjacent to said tissue and cells until said tissue and cells are dislodged by the suctioning force; and (c) a physiological solution to preserve said tissue and cell samples colelcted in said container.

26. The kit of claim 25 wherein said physiological solution is a balanced physiologic salt solution.

27. The kit of claim 25 wherein said kit further comprises in combination an anesthetic in an original container suitable for anesthetizing said area of skin of the body into which said hollow needle is to be inserted.

28. The kit of claim 27 wherein said kit further comprises in combination at least one syringe with 2 needles attachable thereto, said syringe with one said needle being capable of the withdrawal of said anesthetic from its original container; and second needle for transfer of said anesthetic to said skin over the area of the body to be biopsied.

29. The tissue biopsy kit of claim 25 wherein said kit further comprises an evacuated-container holder, said holder capable of supporting said evacuated container while said evacuated container is attached to said hollow needle for the suctioning of said tissue and cell samples.

30. The tissue biopsy kit of claim 25 wherein said evacuated container is an evacuated glass tube.

31. The tissue biopsy kit of claim 25 wherein said kit further comprises in combination at least one gauze sponge for arresting the effusion at, or to dry the site of, said biopsy subsequent to the removal of said hollow needle from said needle insertion site.

32. The tissue biopsy kit of claim 25 wherein said kit further comprises in combination at least one alcohol-saturated pad for cleansing said skin at the site of said biopsy.

33. The tissue biopsy kit of claim 25 wherein said kit further comprises in combination at least one sterile adhesive bandage, for use in protecting said biopsy site from infection.

34. The tissue biopsy kit of claim 25 wherein said kit further comprises in combination at least one fenestrated drape for use as a shield for said area of the body.

35. The tissue biopsy kit of claim 25 wherein said hollow needle is 20 to 22 gauge.

36. The kit of claim 27 wherein said anesthetic is xylocaine.

* * * * *